US008279226B2

(12) United States Patent
Krieftewirth

(10) Patent No.: US 8,279,226 B2
(45) Date of Patent: Oct. 2, 2012

(54) VISUALIZATION OF A PARAMETER WHICH IS MEASURED ON THE HUMAN BODY

(75) Inventor: Michael Krieftewirth, Ersigen (CH)

(73) Assignee: Roche Diagnostics International AG, Rotkreuz (CH)

( * ) Notice: Subject to any disclaimer, the term of this patent is extended or adjusted under 35 U.S.C. 154(b) by 261 days.

(21) Appl. No.: 12/636,313

(22) Filed: Dec. 11, 2009

(65) Prior Publication Data

US 2010/0141656 A1    Jun. 10, 2010

Related U.S. Application Data

(63) Continuation of application No. PCT/CH2008/000222, filed on May 15, 2008.

(30) Foreign Application Priority Data

Jun. 15, 2007  (CH) ..................................... 0966/07

(51) Int. Cl.
  *G06T 11/20*   (2006.01)
  *G09G 5/00*   (2006.01)
  *A61B 5/145*   (2006.01)

(52) U.S. Cl. ................... 345/440.1; 345/440.2; 600/635

(58) Field of Classification Search ............... 345/440.1, 345/440.2
  See application file for complete search history.

(56) References Cited

U.S. PATENT DOCUMENTS

| 5,822,715 | A | 10/1998 | Worthington et al. |
| 2004/0153257 | A1 | 8/2004 | Munk |
| 2007/0128682 | A1 | 6/2007 | Rosman et al. |
| 2007/0135944 | A1* | 6/2007 | Schmid et al. ................. 700/83 |
| 2009/0113295 | A1* | 4/2009 | Halpern et al. ............... 715/273 |

OTHER PUBLICATIONS

PCT Search Report from corresponding PCT/CH2008/000222 mailed Aug. 27, 2008.

* cited by examiner

*Primary Examiner* — Jeffery A Brier
(74) *Attorney, Agent, or Firm* — Roche Diagnostics Operations, Inc.

(57) ABSTRACT

In a method for visualization of a parameter which is measured continuously on or in a human body, in particular a glucose concentration, the following steps are carried out. First, a measured value range for a measured parameter is subdivided into two or more sub-ranges. Trend information is then calculated relating to the future expected profile of the measured parameter on the basis of two or more measured values. A time period after which it is predicted that the measured parameter will have left its current sub-range is calculated based on current value of the measured parameter and the calculated trend information and finally the time period is displayed. On the basis of the calculation and display of a time period after which the measured parameter will have departed from one sub-range to another, it is possible for a patient to assess, even without detailed knowledge of the medical relationships, the effects of his action at a time which he can comprehend on the basis of the prognoses available to him, and if appropriate to take corrective actions. An apparatus for carrying out a method such as this comprises a measurement apparatus, a system controller with a computer having a memory unit and a display. A computer program product for carrying out a method such as this on an appropriate apparatus is likewise disclosed.

14 Claims, 2 Drawing Sheets

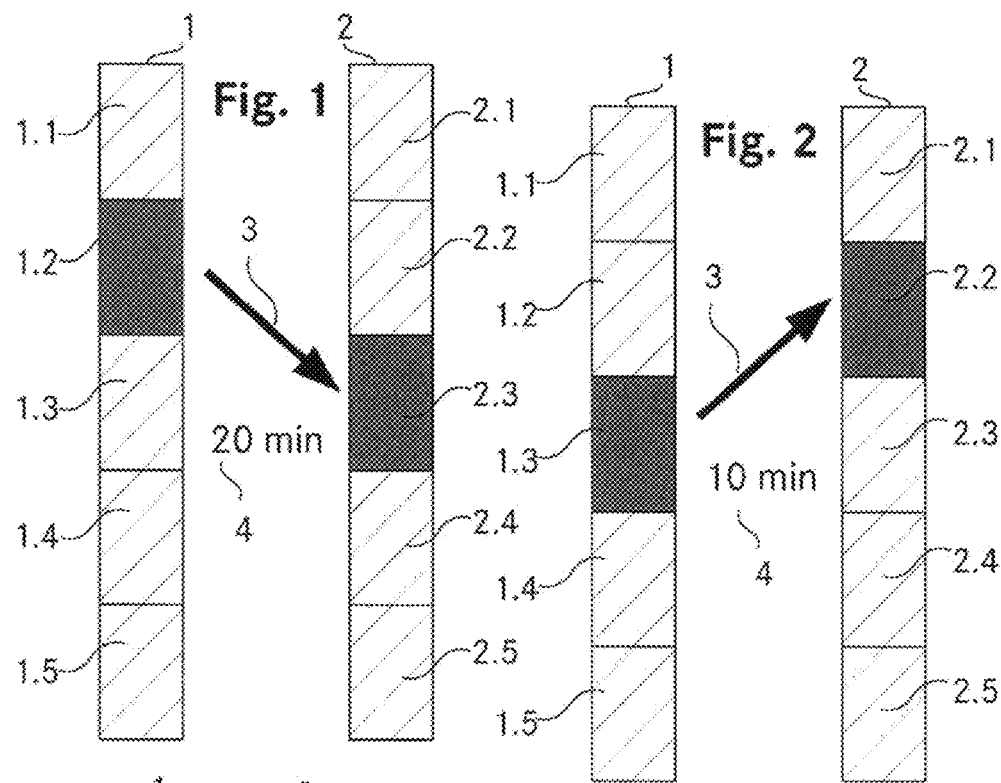
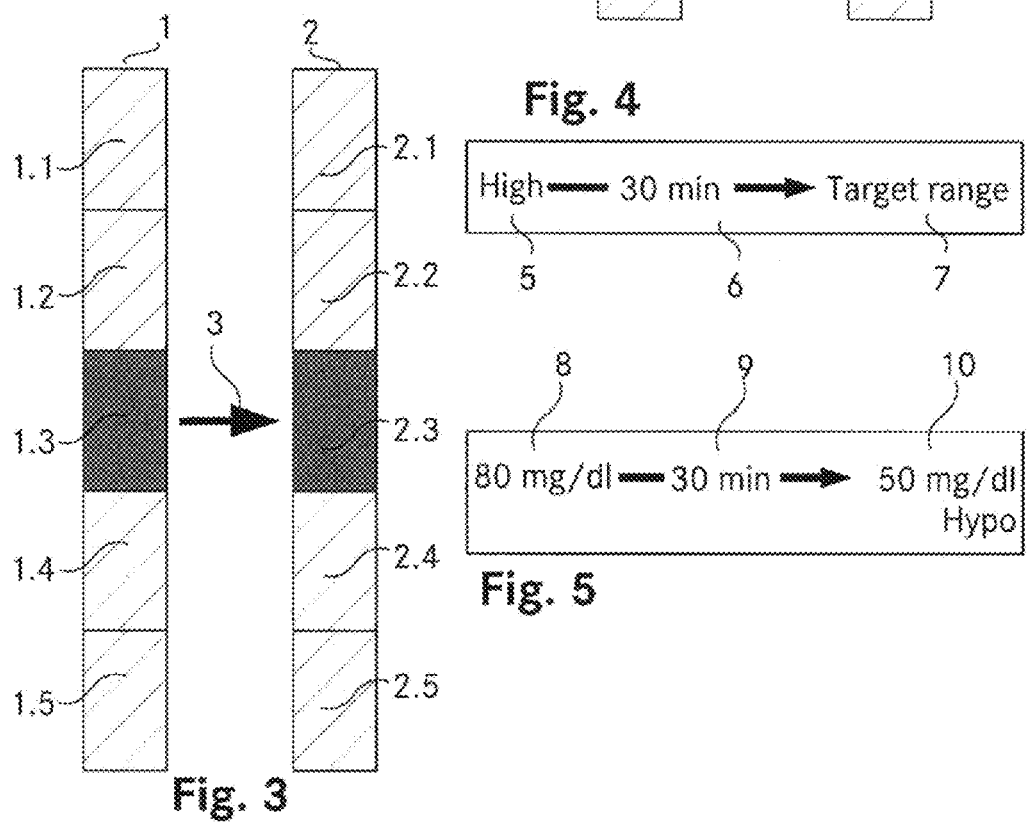

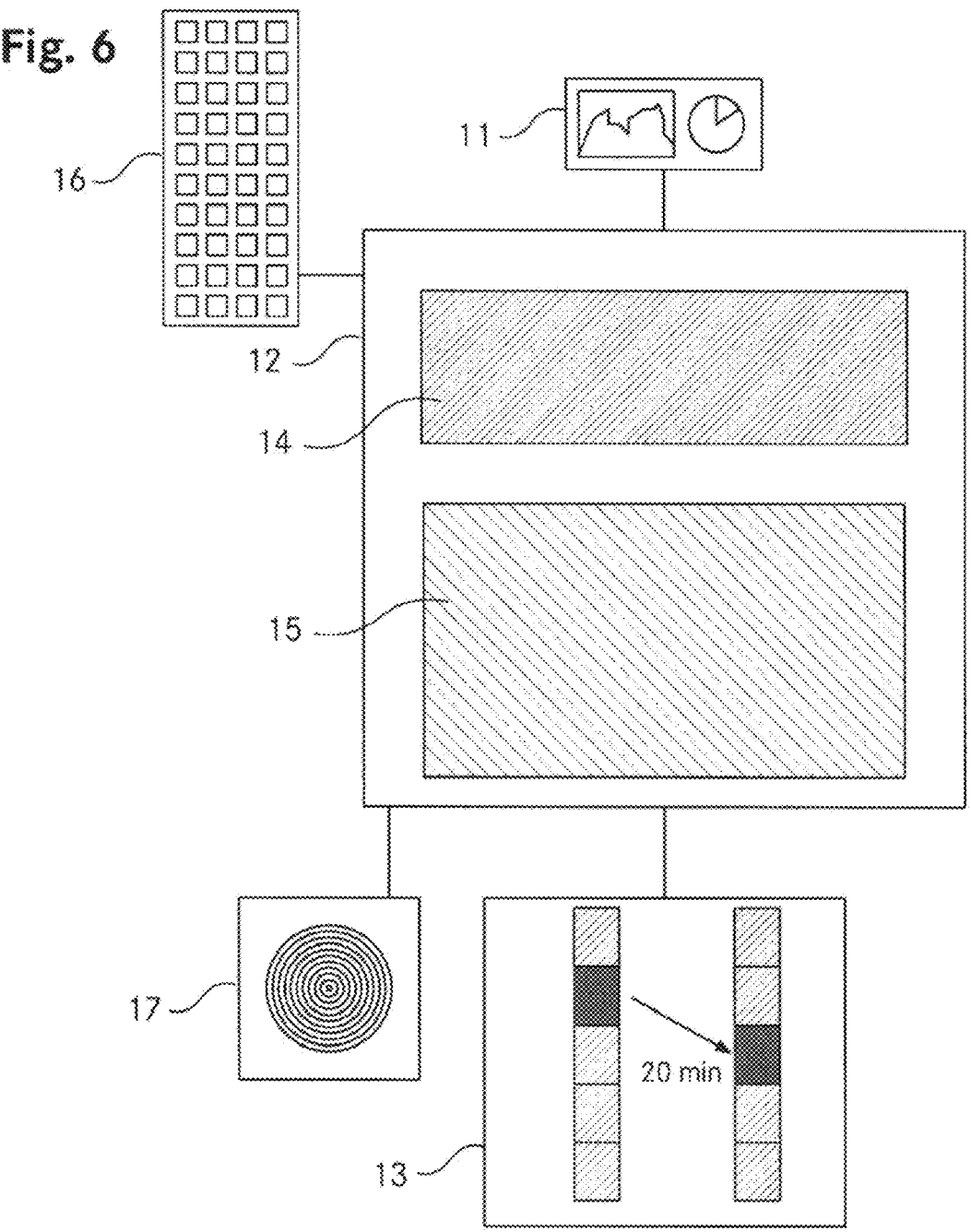

VISUALIZATION OF A PARAMETER WHICH IS MEASURED ON THE HUMAN BODY

REFERENCE

This application is a continuation of PCT/CH 2008/000222 filed May 15, 2008 which is based on and claims priority to Swiss Patent Application No. 966/07 filed Jun. 15, 2007, which are hereby incorporated by reference.

FIELD

This disclosure relates to a method for visualization of a parameter which is measured continuously on or in a human body, in particular a glucose concentration. The disclosure also relates to an apparatus and to a computer program product for carrying out the method.

BACKGROUND

The body of a person who is suffering from diabetes is unable to produce an adequate amount of insulin, or the body does not react reasonably to the insulin produced by him. This fact leads to an imbalance in the glucose concentration in the blood (and thus to hyperglycemia or hypoglycemia), which can result in serious consequences, such as cetoacidosis, complications of the blood vessels, cramps or loss of consciousness. In order to maintain a healthy blood glucose level, diabetic patients normally follow strict dietary programs and link these with the giving of basal insulin and selective insulin boluses. The administration of insulin must be individually matched to the patient's body in order to supply it with the correct amount of insulin at the correct time. In order to determine the time and amount of the next insulin bolus, patients regularly measure the glucose concentration of their blood and determine the carbohydrate content of their meals.

Instead of carrying out the glucose measurements using strip-based measurement devices, as is done at three to six times by day, and in exceptional cases ten or more times per day, depending on the intensity of the therapy being carried out, it is possible to use continuously operating blood glucose measurement devices. One of the advantages of a continuously operating measurement system is the capability to calculate trend information, which can be done in a worthwhile manner only if the measurement data rate is high. The calculated trend information in this case generally relates to the previously measured values and therefore provides information about the profile of the glucose concentration in the near future. External influences such as the administering of an insulin bolus, consumption of meals or sporting activities influence the accuracy of the trend information. The accuracy of the trend calculation can be increased considerably by feeding information about these external influences to a measurement system thus, in particular, also making it possible to match the dosage of an insulin bolus more accurately to a patient's needs.

The calculated trend information relating to the measured parameter, such as a blood glucose concentration, has until now been indicated, for example, by arrows which represent the trend in the sense of it rising, falling or being constant. An upgraded display of the trend, which provides a finer graduation of the rising or falling states in the form of quickly rising, slowly rising, etc. and quickly falling, slowly falling, etc. is likewise known in the form of arrow alignments which can be distinguished from one another.

In addition to the abovementioned display of calculated trend information, it is also known for level information relating to the measured parameter to be displayed, with the measured value range of the glucose measurement device being subdivided into three or more levels. In this case, each level generally represents a physiologically relevant range, such as the hypoglycemic or hyperglycemic range, or a target value range.

The disadvantages of these known forms of display are, inter alia, that arrow information on the one hand gives only an inaccurate and incomplete picture, while more accurate measured value details are in general less useful for the patient, because of lack of specialist knowledge. Furthermore, an indication of level information likewise represents an incomplete picture because these generally represent an instantaneous record and do not provide a historical record of the measured profile of the values. In brief, the previously known forms of display provide the available information inaccurately, incompletely or else in a highly abstract form, and therefore in a form which it is very difficult for the average patient to understand. This is particularly true because the correct interpretation of the corresponding measured variables, which are associated with units such as mg/dl/min, mg/dl/h and the like, in their own right require further understanding of the processes taking place in the body.

SUMMARY

Embodiments of the invention provide a method associated with the technical field mentioned initially, as well as an apparatus, which make it possible for a patient to correctly assess his current physiological situation, with respect to its expected development.

Embodiments of the invention take a measured value range for the measured parameter, in particular the glucose concentration is subdivided into two or more sub-ranges, trend information relating to the future expected profile of the measured parameter is calculated on the basis of two or more measured values. In this case, the calculation can optionally be made more precise by entering additional information relating to the events which influence the measured parameter.

Additional information relating to the events which influence the measured parameter may, for example in the situation in which the measured parameter is a glucose concentration in a person's blood, be the nature, time or for example the carbohydrate content of a meal that has been consumed, an insulin bolus that has been given or the nature and duration of a sporting activity that is being carried out.

A result value, such as a sub-range reached or a time period, is determined on the basis of the calculated trend information, the current value of the measured parameter and a definable input value, such as a time period for a defined sub-range to be reached or to be left, for example.

In one embodiment, a time period is determined after which it is predicted that the measured parameter will have left its current sub-range or will have reached a defined sub-range, with the time period being based on the current value of the measured parameter and the calculated trend information. The time period determined in this way is then displayed.

In another embodiment, a defined sub-range is determined, within which it is predicted that the measured parameter will be after a defined time period, with the sub-range being determined on the basis of a current value of the measured parameter and the calculated trend information.

For average patients, details of measurement variables generally contain little useful information, because this information is worthwhile only in a specific medical overall context of the measured parameter, together with other, for example physiological, values. In contrast, for example, one variable with which the average patient is familiar is represented by a time period. Indication of a time period, after which it is predicted that the measured parameter, for example the glucose concentration, will have left the current sub-range of a plan which the patient can understand and will have entered the next defined sub-range, allows the patient to assess his own physiological situation considerably better. Therefore, in a first embodiment, a current measured value and calculated trend information are used to determine a time period after which the measured parameter, such as the glucose concentration, will have reached a specific measured value. In the second embodiment, a current measured value and calculated trend information are used to determine a measured value and/or a sub-range associated with this, which the measured parameter, such as the glucose concentration, will have reached after a specific time period. The calculated measured values in this case depend on the subdivision of the measured value range.

The current sub-range, the time period until the current sub-range is left and the next defined sub-range which will be reached after the current sub-range has been left are in this case preferably displayed at the same time. This form of display of the method allows the patient to assess his situation particularly well because all of the data required for this assessment can be checked at a glance.

In a further embodiment, a defined time period, a current measured value and calculated trend information are also used to predict the glucose concentration at the end of the time period. This predicted glucose concentration is in this case associated with a defined sub-range in the plan and is indicated.

It is likewise feasible to display individual ones of the three components mentioned above on their own or in conjunction with just one further component, such as an indication of the current sub-range together with the time period before this current sub-range will have been left.

The measured value range is subdivided into different sub-ranges with the assistance of specific limit, threshold or target values for the measured parameter. For example, the glucose limit concentrations for hypoglycemia and hyperglycemia mark sensible values for subdivision of the measured value range since they are associated with specific body states which are relevant for diabetes therapy purposes. The patient can therefore tell particularly quickly whether he is in a healthy state, or his blood glucose concentration is too high or too low.

Alternatively, the measured value range can also be subdivided on the basis of other criteria. For example, the measured value range can be subdivided into sub-ranges of uniform size and with uniform distribution, which are not based on any medically therapeutic principle, but purely, for example, on a numerical principle.

Furthermore, one particularly embodiment of the invention allows user-controlled and user-defined subdivision of the measured value range into individual sub-ranges. This allows the method to be used more flexibly, by the capability of matching widely different requirements, medical situations and individual characteristics.

However, the subdivision of the measured value range can also be preset, this not being disadvantageous in situations in which specific limit, threshold and target values are not distinguished individually, but are generally applicable. This may be the case in particular for absolute limit and threshold values.

The trend calculation can be carried out by evaluation of at least two measured values at different times, in particular by filtering with an output or calculation on a first time derivative or by a first derivative of a function which is matched to the measured values, preferably using a Kalman filter or a spline function. For trend calculation of individual measurement points, it is worthwhile considering two measured values at different times, and making a prediction of subsequent measured values from the development of the measured values. If a sufficiently large number of measured values and an adequate value density are available, it is also worthwhile describing the profile of the measured values by a function which is matched to the values such as a spline function. The functional relationship between measurement values and the time of the measurement allows derivation of the function which describes this relationship, and is advantageously used for trend calculation.

It is also possible to use other methods that are known in principle for measured value approximation by means of one or more functional relationships. These may vary depending on the application, to the extent that adaptations may be required which on the one hand are particularly accurate and computation intensive and, in contrast to this, on the other hand are particularly fast and efficient.

The trend calculation can also take account of a measured value profile which is higher than the first derivative and in particular using suitable filter algorithms or a function which approximates the measured values. The assumption of a constant trend, which is implicitly included in the use of the first derivative of a function, can be weakened by consideration of further derivatives. This leads to a further improvement in the prediction accuracy.

However, if there are only small variations in the trend, it might also be worthwhile using only the first derivative, or a trend indication determined in some other way, ignoring the additional influences such as those described by a second derivative, since this involves less computation effort. The greater the time period over which data is recorded for trend calculation, the more accurate the resultant predictions may be.

If a large number of measured values are recorded, it is possible to estimate more accurately how stable the profile of the measured parameter is and the discrepancies which must be expected in the trend details. An estimate such as this can therefore provide an error to be expected in the prediction and can therefore form a good basis for the decision on the required computation complexity. The length of the time period over which the data is recorded may, for example, depend on the width of the individual sub-ranges of the measured value range if, for example, measured values remain in a wide sub-range with the same value development for longer than in a narrow sub-range.

Subdivision of the measured value range into physiologically relevant sub-ranges has the advantage that this allows a warning to be provided on the basis of the calculated time period before a corresponding sub-range is entered, before this occurs. In many cases, for example, the physiological glucose value ranges such as the hypoglycemic or hyperglycemic ranges resulting in an alarm, for example, must be avoided in any case while, in contrast, the precise profile of the glucose value within the physiologically non-critical range is of secondary importance.

An additional subdivision of a physiologically non-critical range into further sub-ranges is, however, to allow a patient to assess his situation more accurately. This may be based on more stringent requirements for a patient to check his glucose concentration and thus to narrow the margin of the glucose concentrations that are classified as "good", without indicating a dangerous situation.

A warning such as an alarm can be emitted when a measured parameter reaches a defined value such as a critical value. In this case, in particular, the warning may be emitted without any active check. The emission of a warning based, for example, on audible means also informs the user of critical situations in good time without any regular active check. It is likewise possible to emit an appropriate warning in response to an active check, in order to underline the importance of the output value.

It is likewise feasible for a warning to be emitted during and after a defined and in particular a critical value of a measured parameter is reached. This avoids the need for a prior warning time period. A prior warning period in the form of "virtual critical" values could be provided on reaching defined values which are adjacent to critical values but are not yet in their own right critical. This warning can also be provided visually, for example by coloring the display of the sub-ranges using green, yellow and red for "non-critical", "virtually critical" and "critical" sub-ranges. If no warning is emitted, it is the responsibility and the problem of the user to regularly check the measured parameter and its predicted trend.

A request for corrective action can be produced before the defined value, in particular the critical value, is reached. This request may be coupled to the emission of a warning, or may be independent of it. The request for a corrective action is accompanied, in addition to indication of an imminent defined or critical value, by information that the patient should take measures to avoid a critical value. The request for corrective action may also include information as to how it is possible to avoid reaching the critical value. In this case, options include not only general advice such as "reduce your glucose concentration" but also a proposal for a specific action such as "give yourself an insulation bolus of quantity X" or "consume an amount X of carbohydrates".

The request for a corrective action is particularly worthwhile when the physiological situation would deteriorate significantly if a defined value were to be reached, overshot or undershot, in the sense of a medically critical state. The need for a corrective action is implicitly signaled to the patient just by the indication of the current physiological situation and its expected development. An explicit request should in fact therefore be regarded as a further feature to assist the patient.

An apparatus for carrying out a method which can be described as above comprises a measurement apparatus for continuous measurement or feeding of a parameter which is measured on or in a human body, in particular a glucose concentration. Embodiments of the invention also comprises a system controller having a computer for the calculation of trend information about the future expected profile of the measured parameter, and for production of a prediction for a result value based on an input value, in particular such as a time period within which the measured parameter will reach a predeterminable value, or a sub-range which the measured parameter will reach after a predeterminable time period. The system controller also includes a memory unit for storage of the measured value range subdivision, the parameters and measured values fed in and, furthermore, a display. In this case, the system controller is designed and programmed such that the measured value range of the measurement apparatus can be subdivided into at least two sub-ranges, and such that a result value, in particular a time period after which it is predicted that the measured parameter will have left its current sub-range, or a sub-range which it is predicted that the measured parameter will reach after a predeterminable time period can be determined. In this case, the result value is determined on the basis of the current value of the measured parameter, the calculated trend information and the input value. In this case, the determined result value can be output via the display.

The apparatus according to embodiments of the invention advantageously comprises all the abovementioned elements in order to allow it to operate as a functional unit. At least the system controller must be able to have or address appropriate, input and output apparatuses. It is therefore not absolutely essential for a measurement apparatus to be part of the apparatus according to the invention. However, an apparatus must be provided to allow a parameter to be fed in. An analogous situation applies to the output of the data which in fact controls a display contained in the apparatus according to embodiments of the invention. However, in principle, all that is required is an apparatus for transmission of data to a display unit, in particular an external display unit.

The above mentioned apparatus has an input apparatus which allows a user to interact with the system controllers. An input apparatus such as this extends the range of application of the apparatus to those methods which envisage interaction with the user and can or must be individually adapted.

Without an input apparatus, the system controller must be set in a relatively general form in order to largely comply with the needs of every user. It may also be advantageous to allow only specific data items to be edited by a user, specifically those data items which differ individually, in contrast to data or settings such as limit and threshold values, which are considered to be generally applicable.

Furthermore, the abovementioned apparatus can include an alarm transmitter which warns a user before a defined and in particular critical value of the measured parameter is reached. A warning such as this may also be emitted by means of the alarm transmitter without any active check by the user. An alarm transmitter which is provided in addition to a display relieves the user of the task of regularly checking the apparatus and actively monitoring whether, for example, the glucose concentration is approaching a critical value.

A non-transient computer program product which processes data from a measurement, which is carried out continuously on or in a human body, of a parameter, may be used to carry out one of the methods mentioned above. In this case, the measured parameter may, in particular, describe a glucose concentration. Furthermore, the measured value range of the measured parameter is subdivided into sub-ranges, and trend information about the future expected profile of the measured parameter is calculated from the measured data. A result value, in particular a time period after which it is predicted that the measured parameter will have left its current sub-range or a sub-range which it is predicted that the measured parameter will reach after a predetermined time period is determined, based on a current value of the measured parameter, the calculated trend information and a predeterminable input value. This determined result value is then provided as the output.

Further advantageous embodiments and feature combinations of the invention will become evident from the following detailed description and the totality of the patent claims.

BRIEF DESCRIPTION OF THE DRAWINGS

In the drawings which will be used to explain the exemplary embodiment:

FIG. 1 shows an illustration in the form of a graph of the measured value range, subdivided into sub-ranges, with a falling trend;

FIG. 2 shows an illustration in the form of a graph of the measured value range, subdivided into sub-ranges, with a rising trend;

FIG. 3 shows an illustration in the form of a graph of the measured value range, subdivided into sub-ranges, without any identifiable rising or falling trend;

FIG. 4 shows a text display of the measured value range, subdivided into sub-ranges, for a falling trend;

FIG. 5 shows a number display of the measured value range, subdivided into sub-ranges, for a falling trend; and FIG. 6 shows an apparatus for carrying out a method for visualization of a parameter which is measured on or in a human body.

Fundamentally, identical parts are provided with the same reference symbols in the figures.

DETAILED DESCRIPTION

FIG. 1 shows a measured value range 1, which is subdivided into sub-ranges 1.1-1.5, for measurement of a parameter which is measured on or in a human body, in particular a glucose concentration in a person's blood emphasizing a sub-range 1.2 in which the current measured value is located. The illustration in the form of a graph of the measured value in this form directly indicates to a patient where the current measured value can be positioned with respect to the entire measured value range. In addition, a second measured value range 2 is shown, which is likewise subdivided into sub-ranges 2.1-2.5 and in which the sub-range 2.3 is emphasized, in which the predicted measured value, for example the glucose concentration, will next occur. Each of the sub-ranges 1.1-1.5, 2.1-2.5 indicates an interval of the entire measured value range 1, 2, with the respective sub-range 1.2, 2.3 within which the result of the current or a future measurement, respectively, is or will be, being emphasized in the graph. The two illustrations of the measured value ranges 1 and 2 show the same measured value range, which has also been subdivided in the same way, at different times. In this case, the measured value range 1 forms an illustration of the current measurement, while in contrast to this the measured value range 2 shows a predicted measurement with the same subdivision. An arrow 3 in FIG. 1 is also shown between the emphasized sub-ranges, illustrating the fact that the glucose concentration will change towards lower values. Furthermore, the time 4 of 20 minutes is indicated, for which the change from the current sub-range 1.2 to the other sub-range 2.3 is predicted. The indication of the time period makes it possible for the patient to estimate his physiological situation particularly well because, in contrast to medical or technical details, time periods are known from daily life by any average patient.

In a first operating mode, a time 4 before the condition occurs is determined and indicated on the basis of a current value of the measured parameter, which is associated with a first sub-range 1.2, and the calculated trend information, and subject to the condition that the measured parameter will leave the current sub-range and will reach a second sub-range.

In a second operating mode, a predicted value of the measured parameter is determined on the basis of a current value of the measured parameter which is associated with a first sub-range 1.2, and the calculated trend information and subject to the condition that a specific time 4 will pass, and this measured parameter is associated with a second sub-range 2.3. In this case, the sub-ranges and the time period are displayed analogously to the first operating mode, in which a time 4 is calculated for which a change in the measured parameter from a first sub-range 1.2 to a second sub-range 2.3 is predicted.

FIG. 2 likewise shows a measured value range 1, which is subdivided into sub-ranges 1.1-1.5, of the measurement for example of the glucose concentration in a person's blood, with the sub-range 1.3 within which the current measured value is located being emphasized. FIG. 2 also shows a second measured value range 2 which is subdivided into sub-ranges 2.1-2.5 and in which the sub-range 2.2 within which the predicted glucose concentration will occur is emphasized. As in FIG. 1, an arrow 3 is also shown between the measured value ranges 1 and 2 in this case, indicating that the glucose concentration will rise. The time 4 of 10 minutes which is predicted before the change between the sub-ranges 1.3 and 2.2 will occur, or which is defined as the prediction time period, is also indicated.

If the system according to the invention does not find any clearly rising or falling trend in the glucose concentration, but predicts a stagnation in the glucose concentration, the arrow 3 neither rises nor falls, but is aligned horizontally, as illustrated in FIG. 3. The indication of a time after which a change in the sub-range would occur is in this case obviously not worthwhile. The time indication can therefore be omitted when the glucose concentration is constant, or can be replaced by information corresponding to the situation. The time when the glucose concentration is considered to be constant depends on an entered or preset maximum time. Time periods for the change between adjacent sub-ranges which are greater than this minimum time by definition lead to a classification of the trend as constant. The choice of the maximum time may in this case depend on the individual patient, or else be predetermined.

In addition to the display as has been demonstrated in the previous figures, the measurement of a parameter can also be displayed in the form of text, for example in the case of the glucose concentration. A text display of this kind is shown in FIG. 4 that shows an actual state "high" 5 and a predicted state "target range" 7, for which the time 6 of 30 minutes has been calculated in order to reach the state 7, and this is likewise indicated. In particular, the text display is intended to be able to display information at a qualitatively descriptive level. As an alternative to a text display, easily comprehensible symbols, in particular smiley faces, can also be used. This may be particularly advantageous when a diagrammatic representation as in FIG. 1 to 3 would be rather confusing for patients or when only small-format display units are available. In addition, the text display is also very highly suitable for making statements about the physiological state of the patient from the medical point of view, such as "critical" or "normal" etc.

FIG. 5 shows a numerical display of the measured glucose concentration and of the predicted trend of the glucose concentration. An actual state 8 of 80 mg/dl is indicated as the objective value. The predicted state 10 of 50 mg/dl with "hypo" as an indication of critical hypoglycemia is indicated alongside this, and provides assistance to the patient, particularly in critical situations in interpretation of the numerical value. The time 9 of 30 minutes which will pass, according to the calculations, before the predicted state 10 is reached, is likewise displayed.

Both the text display and the numerical display or pure graphical reproductions of the information relating to the measured and the predicted glucose concentration additionally offer the capability to output an alarm. This alarm may preferably be output in audible form, or in audible and visual form. In particular, visualizations such as flashing symbols, the use of warning colors, particularly large or conspicuous characters or the like, are particularly suitable as a visual alarm. Audible warnings can be provided by emitting a warning signal, in particular in the form of a sequence of different tones or an intensive continuous tone. In this case as well, it is possible to use in principle known audible warning mechanisms.

It is particularly useful in this context to emit a proposal for a countermeasure, in order to prevent the occurrence of a critical situation. In particular, this may be coupled to the emission of an alarm. Together with information about a critical situation, a corrective action to avoid this situation can therefore be proposed, such as giving a specific dose of insulin or ending a stressful or potentially hazardous activity of the patient, for example sport or car driving.

FIG. 6 shows an apparatus according to the invention. A continuously operating measurement apparatus 11 measures a parameter on or in a human body, in particular a glucose concentration. The measurement apparatus 11 feeds the recorded data to a system controller 12 which contains at least one computer 14 for calculation of trend information from the previous profile of the measured parameter, possibly assisted by the input of additional information, in particular diabetes-relevant information such as meal times or insulin boluses, and for production of a prediction for a time period within which the measured parameter will vary by a predeterminable value. The system controller 12 also includes a memory unit 15 for storage of the measured value range subdivision and of the parameters and measured values fed in. The system controller 12 reproduces the calculated and processed data on a display 13, which on the one hand displays a current measured value and on the other hand a predicted measured value, as well as a time which it is predicted will pass before the predicted measured value is reached.

The apparatus illustrated in FIG. 6 also has an input apparatus 16 by means of which a user can influence, vary and/or enter a number of functions of the apparatus, as well as individual parameters. Inter alia, the variable functions may be the recordings of data and its storage as well as the input of parameters for the calculations, in particular the desired accuracy of the calculation. The subdivision of the measured value range into sub-ranges and the display form of the recorded and calculated data and possible limit, target or threshold values of the measured parameter, for example of the glucose concentration, furthermore represent further variable parameters. In addition, the apparatus has an alarm transmitter 17 which can make the user aware of an imminent critical situation, for example by audible or visual signals. For this purpose it can output a signal, for example, a specific time before a critical situation is reached, that is to say for example before a sub-range is reached with contains critical glucose concentrations. Critical glucose concentrations such as these may in particular be those which indicate hyperglycemia or hypoglycemia. Because the apparatus according to the invention is able to calculate a relatively accurate prediction about an expected development of the glucose concentration, it can be used to provide a sufficiently early warning of the occurrence of a critical glucose concentration.

Ideally, a warning such as this is provided at a time which can be understood by a patient. This can be done in some cases by observation of the development of the trend of the glucose concentration, because a change in the trend can lead to the deduction of a physiologically relevant event. If the currently measured glucose concentration is in a sub-range which is adjacent to a critical sub-range, a change in the trend towards this critical sub-range will lead to a warning being emitted. In this case, this warning is preferably emitted irrespective of a check by the patient. This will at least make the patient more aware of the situation. The request for a corrective action could even make it possible for a patient in this way at least to survive critical physiological situations.

In addition to the abovementioned displays in the form of text, numerical and graphics displays, these elements may also be combined as required. For example, it may be particularly helpful to couple a graphical display to the measured values. This makes it possible for the patient on the one hand to use the graphical display to obtain an intuitively qualitative assessment of his physiological situation, and on the other hand to use the numerical display to also obtain a quantitative assessment of his physiological situation.

In addition, a useful modification of the abovementioned exemplary embodiments is an additional display of therapy-relevant information alongside the measured parameters. Specifically, this may be the time, the time which has passed since then and the nature of the most recently recorded meal times, the time, the time which has passed since then, and the amount of an insulin bolus or a physical activity, both its nature and duration. In this case, the system may know therapy-relevant information, or this can be entered by the user or can be notified to the system.

With regard to the arrows in the graphical display of the trend of the glucose concentration, it is, of course, also possible to distinguish the gradient according to the invention, since this represents the rate of change of the glucose concentration, for example, qualitatively, as is also known from the prior art. This measure is used to assist the perception of the trend of the glucose concentration by the user. The quantitative display in the form of a time period is, however, a major factor for the purposes of the invention. In this case, this quantitative display may assume various forms in addition to being displayed as the time still remaining in minutes or seconds. Possible examples relating to this are a digital or analogue display of the time at which the change between the sub-ranges will take place. Furthermore, the display could be in the form of an hourglass, or a moving bar.

It can be stated that embodiments of the invention provides a method and an apparatus which allow a patient to assess the expected development of his current physiological situation. The solution is based on the calculation and display of a result value, in particular a time period, after which a measured parameter will change from one sub-range to another, or of a sub-range which the measured parameter will reach after a predetermined time period. It is possible for the patient to assess the effects of his action at a time that he can comprehend and on the basis of the predictions available to him, and if appropriate to take corrective actions, without any detailed knowledge of medical relationships.

Thus, embodiments of the visualization of a parameter which is measured on the human body are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for visualization of a glucose concentration which is measured continuously in a human body, comprising the following steps:
   a) subdividing a measured value range for a glucose concentration into two or more sub-ranges that are user-defined to address widely different individual requirements and medical situations;
   b) calculating trend information relating to the future expected profile of the glucose concentration on the basis of two or more measured values;

c) determining a result value, based on a current value of the glucose concentration, the calculated trend information and a definable input value; and d) displaying the glucose concentration current value, trend information, and the result value.

2. The method according to claim 1, characterized in that the definable input value is the sub-range, and the result value to be determined is a time period after which the measured parameter has left or reached the sub-range.

3. The method according to claim 1, characterized in that the definable input value is a time period and in that the result value to be determined is a determined sub-range which the measured parameter will have reached after the definable time period.

4. The method according to claim 1, characterized in that the calculation of trend information over the future expected profile of the measured parameter on the basis of two or more measured values includes additional information relating to events which influence the measured parameter.

5. The method according to claim 1, characterized in that the current sub-range, the time period until this sub-range is left and a next predicted sub-range which will be reached after leaving the current sub-range are displayed at the same time.

6. The method according to claim 1, characterized in that the measured value range is subdivided into sub-ranges by means of limit, threshold and target values of the measured parameter.

7. The method according to claim 1, characterized in that the trend calculation is carried out by evaluation of at least two measured values at different times using a spline function.

8. The method according to claim 1, characterized in that calculating trend information is performed using a spline function.

9. The method according to claim 1, characterized in that the measured value range is subdivided into physiologically relevant sub-ranges.

10. The method according to claim 1, wherein a warning is emitted independently of an active check prior to the glucose concentration reaching a critical value.

11. The method according to claim 10, wherein a request for a corrective action is emitted prior to the glucose concentration reaching a critical value.

12. An apparatus for visualization of a glucose concentration which is measured continuously in a human body, comprising:

a) a measurement apparatus for continuous measurement or feeding of a parameter which is measured on or in a human body, in particular a glucose concentration;

b) a system controller coupled to the measurement apparatus having, a computer for the calculation of trend information about a future expected profile of the parameter which is measured and for determination of a result value, and a memory unit for storage of a measured value range subdivision, parameters fed in and measured values; and c) a display coupled to the system controller; wherein the system controller being designed and programmed such that, d) the measured value range for a glucose concentration of the measurement apparatus are subdivided into at least two sub-ranges that are user-defined to address widely different individual requirements and medical situations;

e) the result value sub-range can be determined on the basis of a current value of the glucose concentration, the calculated trend information and the definable input value time period; and f) the display shows the current value of the glucose concentration, trend information, the result sub-range, and the input value time period.

13. The apparatus according to claim 12, further comprising an input apparatus coupled to the system controller for interaction between a user and the system controller.

14. The apparatus according to claim 12, further comprising an alarm transmitter coupled to the system controller which warns a user prior to the glucose concentration reaching a critical value.

* * * * *